(12) United States Patent
Mukuta (10) Patent No.: US 8,672,909 B2
(45) Date of Patent: Mar. 18, 2014

(54) FAECAL INCONTINENCE COLLECTOR (76) Inventor: Talabushi Akanganyira Mukuta, Gothenburg (SE)

( * ) Notice: Subject to any disclaimer, the term of this patent is extended or adjusted under 35 U.S.C. 154(b) by 0 days.

(21) Appl. No.: 13/510,667

(22) PCT Filed: Nov. 25, 2010

(86) PCT No.: PCT/SE2010/000277
§ 371 (c)(1),
(2), (4) Date: May 18, 2012

(87) PCT Pub. No.: WO2011/065885
PCT Pub. Date: Jun. 3, 2011

(65) Prior Publication Data
US 2012/0245544 A1    Sep. 27, 2012

(30) Foreign Application Priority Data
Nov. 25, 2009  (SE) ...................................... 0901488

(51) Int. Cl.
*A61F 5/44* (2006.01)
(52) U.S. Cl.
USPC ........... 604/347; 604/327; 604/332; 604/333; 604/334; 604/338; 604/339; 604/344; 604/355
(58) Field of Classification Search
CPC ................................ A61F 5/443; A61F 5/457
USPC ......... 604/327, 332–334, 338–339, 344, 347, 604/355
See application file for complete search history.

(56) References Cited

U.S. PATENT DOCUMENTS

| 7,815,618 B2* | 10/2010 | Schena et al. | 604/337 |
| 7,918,836 B2* | 4/2011 | Gill et al. | 604/333 |
| 2006/0111682 A1* | 5/2006 | Schena et al. | 604/334 |
| 2008/0243098 A1* | 10/2008 | Hewitt | 604/355 |

* cited by examiner

*Primary Examiner* — Philip R Wiest
*Assistant Examiner* — Ariana Zimbouski
(74) *Attorney, Agent, or Firm* — Egbert Law Offices, PLLC (57) ABSTRACT The invention relates to an, for patients with faecal/urinary incontinence, auxiliary device in the form of a, on the skin around the anus, glued collection bag made of suitable and skin-friendly plastic that is foldable 180 degrees in the patient's front or back position.
The design eliminates or substantially reduces the direct contact with faeces and thereby reduces the instances of possible contamination.
The collection bag is equipped with channels for water rinsing 9, ointment application 10 and deodorising filters F.
The collection bag can be used continuously for several days. The collection bag can easily be removed from the patient by means of the top 6 being made of light-sensitive adhesives.
When the collection bag is removed, the bag can easily be sealed with the lid 8 and transported by means of the carrying handle 7.

3 Claims, 13 Drawing Sheets

FAECAL INCONTINENCE COLLECTOR

1. TECHNICAL AREA

The above stated invention is for patients with faecal/urinary incontinence. It is an auxiliary device in the form of a collection bag that is glued to the skin around the anus and which is made of suitable and skin-friendly plastic.

The collection bag is designed as a simple, funnel-like bag that has openings at both ends. These ends are easily sealed.

The design eliminates or substantially reduces direct contact with the faeces and thereby reduces the risk of contamination.

The collection bag is equipped with channels for rinsing with water and the application of ointment and odor removal.

This design will allow the collection bag to be used continuously for several days.

The collection bag can be used of both male and female patients with faecal incontinence with no need for any modification. The collection bag may, with some slight modifications, be used for urinary incontinence.

Other areas of use to be considered are heavy menstrual bleeding or bleeding while giving birth.

2. BACKGROUND

Present day collection bags are usually one-use disposable collection bags that are discarded/destroyed after use. These collection bags are sealed only at one end. This results in the unhygienic handling of faeces that increases the risk of contamination.

Previously known collection bags for faecal incontinence are:
- WO 2009/021520 A1 of 2 Feb. 2009 that constitutes a collection bag for multi-day use with an emptying option. This device lacks the possibility for sealing in order to deal with the content in a hygienic manner. It lacks both the ability to rinse the bag and to apply ointment for skin treatment.
- U.S. Pat. No. 7,101,357 B2 of 5 Sep. 2006 shows a collection bag for single use without the possibility for reuse. The possibility to seal and take care of the content in a hygienic manner is completely absent.
- U.S. Pat. No. 5,593,397 of 14 Jan. 1997 shows a collection bag of the traditional model. The bag is completely missing the possibility to "on the spot be emptied and reused." The possibility to seal the bag after use is completely absent. The ability to transport the bag in a hygienic manner is also missing.
- U.S. Pat. No. 4,445,898 of 1 May 1984 describes a collection bag similar to the one outlined above—with the same disadvantages.

These bags use a sealing agent of the traditional type.

To prevent accidental leakage of the collection bag a glue/adhesive of a type that is relatively difficult to remove without the patient feeling discomfort is used.

3. SUMMARY OF THE ABOVE STATED INVENTION

A collecting bag for patients with faecal incontinence, according to the above stated invention, is designed to provide a single, sealable and washable bag that can be used for either several day or one-day use. In addition, the bag allows for drying and the application of skin care products on the patient.

The elongated collection bag is designed so that it can be used by both sexes. With minor adjustment it can also be used for urinary incontinence.

After use, the bag can easily be sealed, and in a hygienic manner can either be designated for disposal or reuse.

The use of light-sensitive adhesive in this invention allows for the painless removal of this collection bag from the patient's body.

4. A SHORT DESCRIPTION OF THE INVENTION

The invention described in this patent claim will sweep aside the aforementioned drawbacks of the known technology.

The collection bag includes a slotted, with glue/adhesive coated, fastening top. The fastening top is joined together with the elongated and funnel-shaped collection bag. The bag is closed with an upside-down funnel-like exit.

The slotted top fastening is, via a strip of suitable length, connected to a lid of similar size (not slotted), intended for sealing the slotted top.

The connection and lid are provided with channels for rinsing with water, drying with hot air, and for the application of skin ointment.

At the point of contact a skin friendly adhesive is situated, the objective of this adhesive is to create an effective seal around the anus opening.

The adhesive agent used in this invention consists of a light-sensitive adhesive/glue, which after illumination loses its adhesive qualities and then releases the bag from the patient's skin without pain and without mess.

The lid is fitted with a skin-friendly adhesive, with slightly lower adhesive qualities.

The lid is used for sealing the slotted top, to allow for the hygienic and contamination safe removal of the collection bag.

Another purpose of the invention is to provide a collection bag that can be attached to the body. The bag's design, compliance and extensibility means that it is stuck on at the time of use, without the patient being exposed to pain or discomfort at the time of placement or removal. Other distinguishing features are that the collection bag is provided with channels for water rinsing, the blowing of hot air, and the application of skin ointment.

The channel for water rinsing can also be used for odorless gas ventilation, using a deodorising filter.

Furthermore, the purpose of the invention is to provide a collection bag whereby the slotted fitting top will automatically fit both male and female patients without any adjustment.

5. BRIEF DESCRIPTION OF THE DRAWINGS

The invention will be further described by way of example, with reference to the attached drawings, where:

The image also shows the de-odorising filter and the sealing cone for the skin ointment channel.

FIG. 19 shows the collection bag glued to a male patient's stomach.

PREFERRED DESIGN FORM ALTERNATIVES

In the following, the preferred design forms of the collection bag, according to the invention, will be described, initially with reference to FIG. 1.

Although the text below refers to the use of the collection bag for faecal incontinence, the invention also relates to the use of the bag for urinary incontinence.

Figure 1:
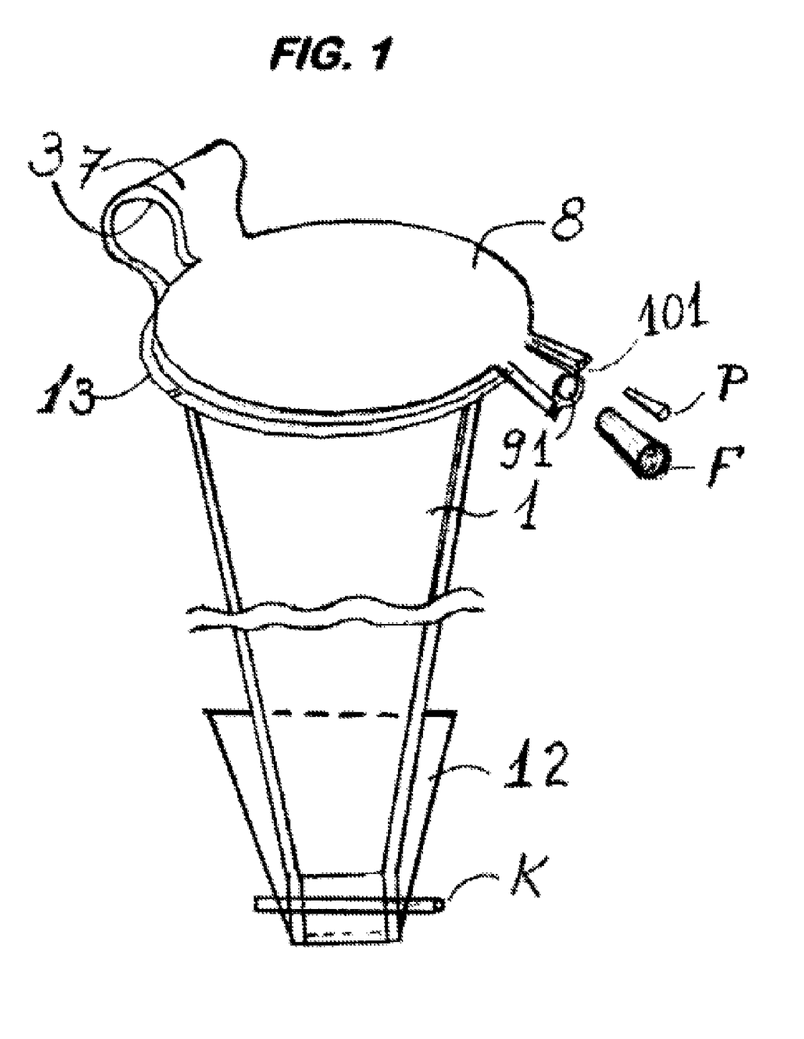
FIG. 1 shows a perspective of the funnel-shaped collection bag with its carrying strap and seal at the bottom together with its plastic clip. At the top the lid is closed. The lid highlights the connection possibilities for water/air rinsing and the application of skin ointment.

FIG. 1 shows the collection bag for faecal/urine collection in position, after the bag has been removed from the patient. Bag 1 is securely sealed with the lid 8. The strap between the top of the bag and the bag's lid 3 or 7 automatically creates a carrying handle for easy and smooth removal of the bag for emptying and possible treatment of the bag for re-use.

When emptying the contents of used collection bag, the user proceeds to connect the bag's funnel-like bottom 12 with the external discharge pipe's cone OFF. The discharge pipe is connected to a closed collection container. The plastic clamp K at the bottom of the bag is removed and the odor removal filter F is also removed. The filter's funnel-shaped channel opening 91 is connected to the water pipe VL enabling rinse water to be supplied. The rinse water may contain disinfectant. After rinsing, the same channel can be used for connecting a hose for hot air drying of the bag and skin.

The above process can be multiplied and relate to the emptying of several bags at the same time. Health-care workers exposure to smell and dirt, etc. are minimized and the risk of infection is eliminated completely with correct use.

Figure 2:
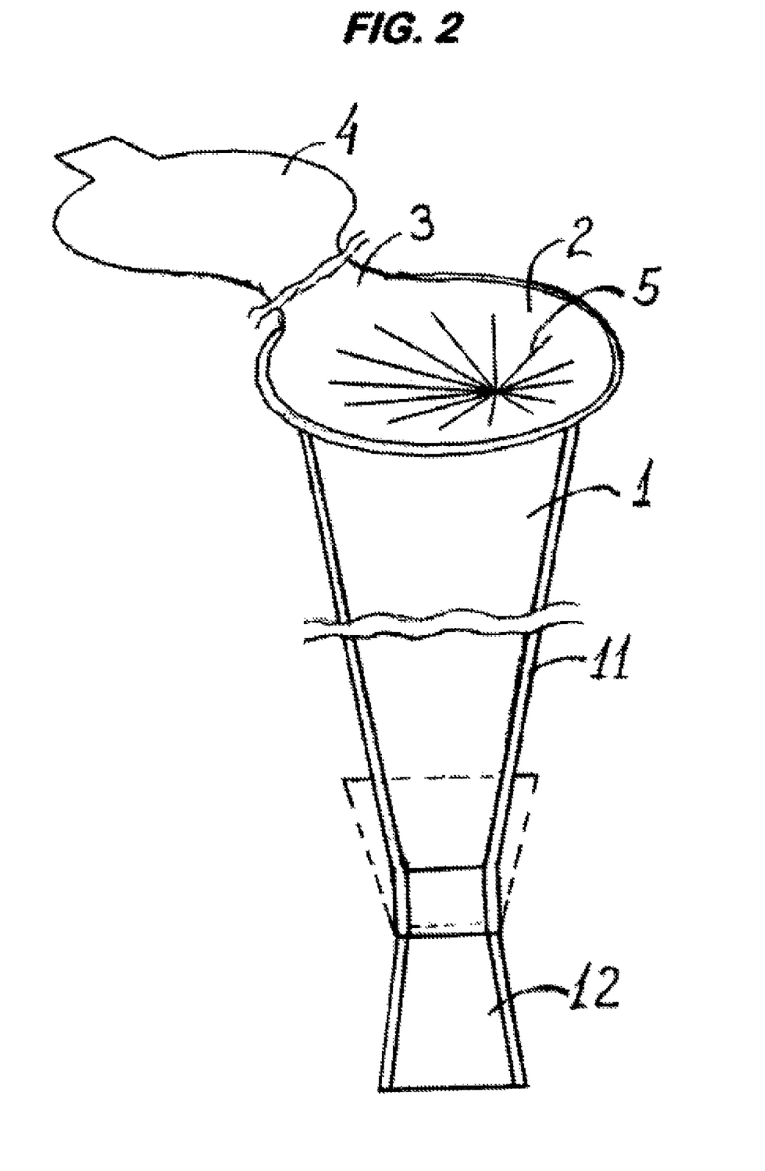
FIG. 2 shows in perspective the collection bag before the initial application with the slotted top and the carrying strap in the open position. The drawing also shows the collection bag with the funnel end shown upside down.

FIG. 2 shows a drawing in perspective, the bag with the slotted top 5, the carrying strap 3 and the lid 4 in open position prior to the bag is being applied to the patient for use. The collection bag in this case shows the simplest implementation of the invention, namely the bag without the rinsing channels. The drawing also shows the connection end with the inverted funnel 12. The funnel 12 provides a secure tightly fitting connection to the discharge pipe, or water pipe VL.

In the funnel 12 is first placed a small plug S of a sponge like plastic with an enclosed air/gas cell, and thereafter the funnel-like end is folded up and secured with a plastic clamp K so that it is squeezed over the sponge to form a tight seal.

Figure 3:
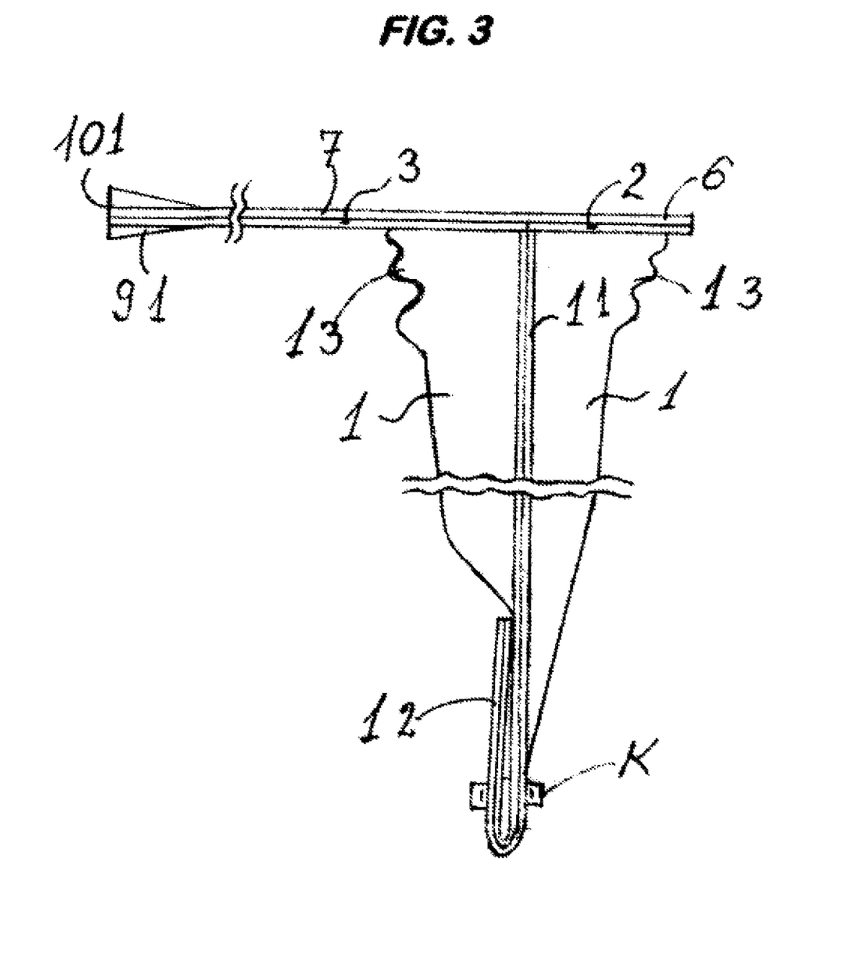
FIG. 3 shows a side view of the bottom, together with a plastic clip, and sealed collection bag.

FIG. 3 shows how the plastic clip is applied to the plastic bag.

Figure 4:
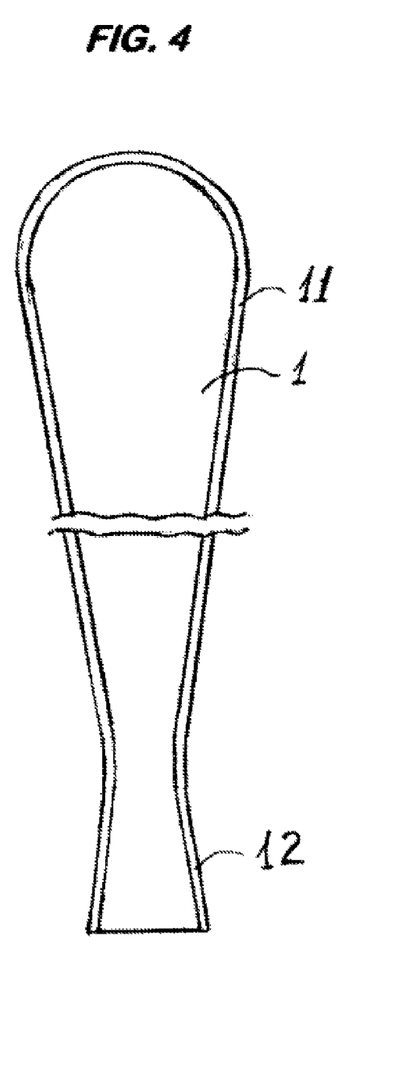
FIG. 4 shows the frontal view of the collection bag.
Figure 5:
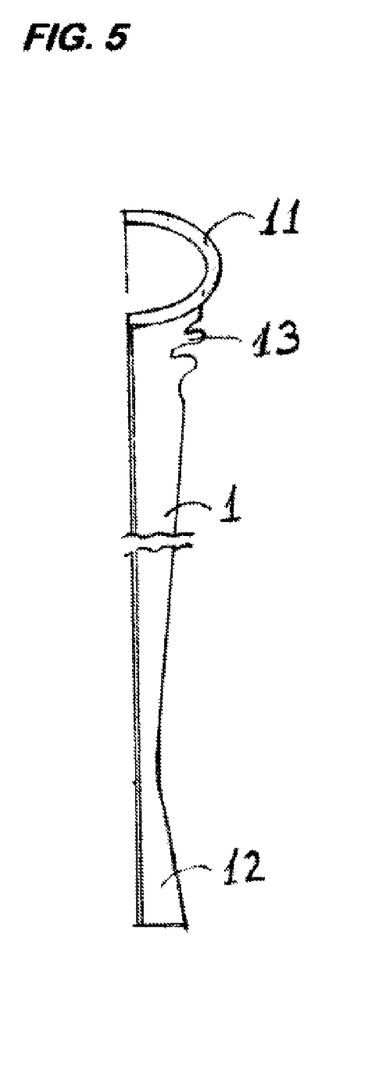
FIG. 5 shows a side view of the collection bag wall folded and prepared for hot-sealing/bonding/gluing.

FIG. 3 also shows the pleated parts 13 on the collection bag which is accomplished by means of welding/gluing the collection bag's plastic sides 1 via the Welded/adhesive surfaces 11 illustrated in FIG. 4 and FIG. 5.

Figure 18:
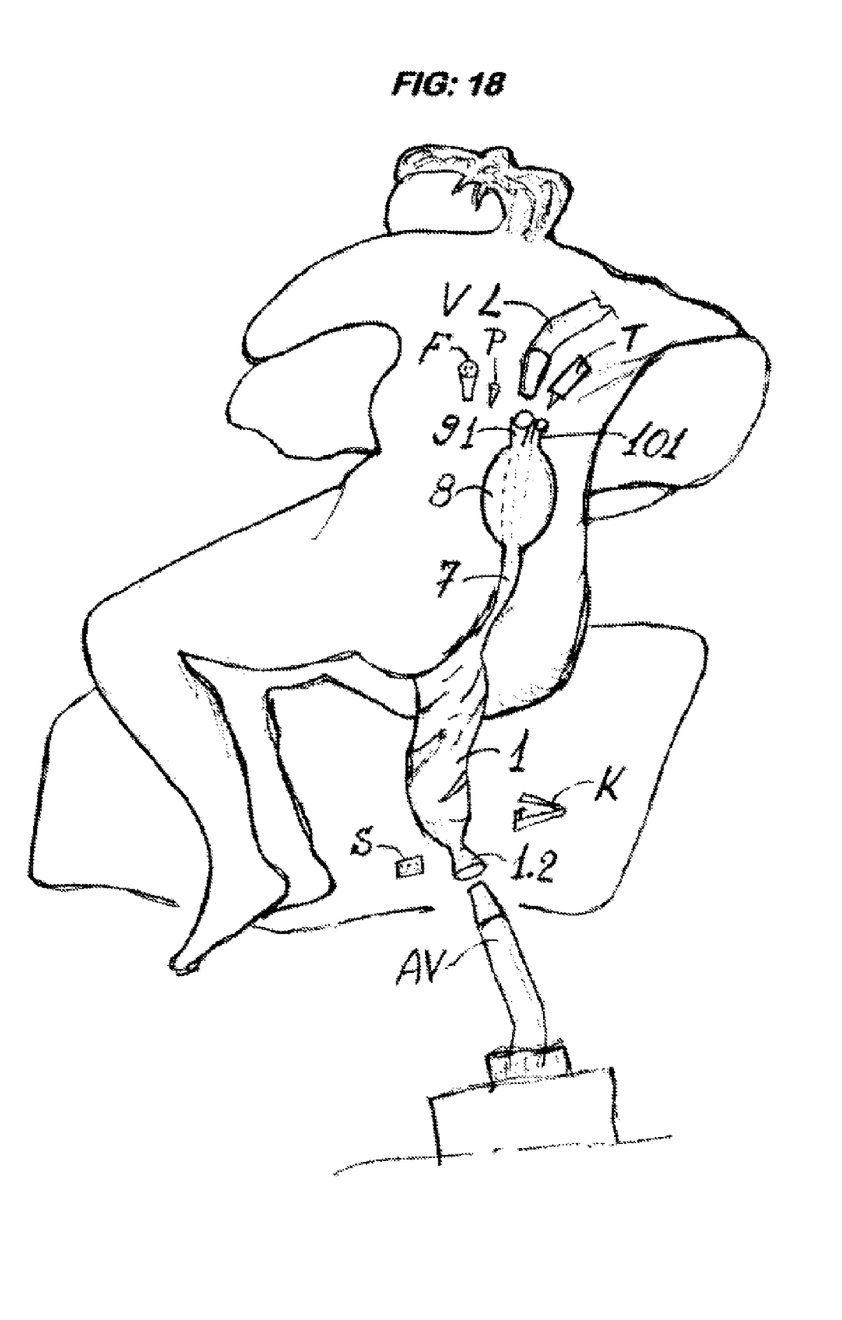
FIG. 18 shows the collection bag's emptying and rinsing.
Figure 20:
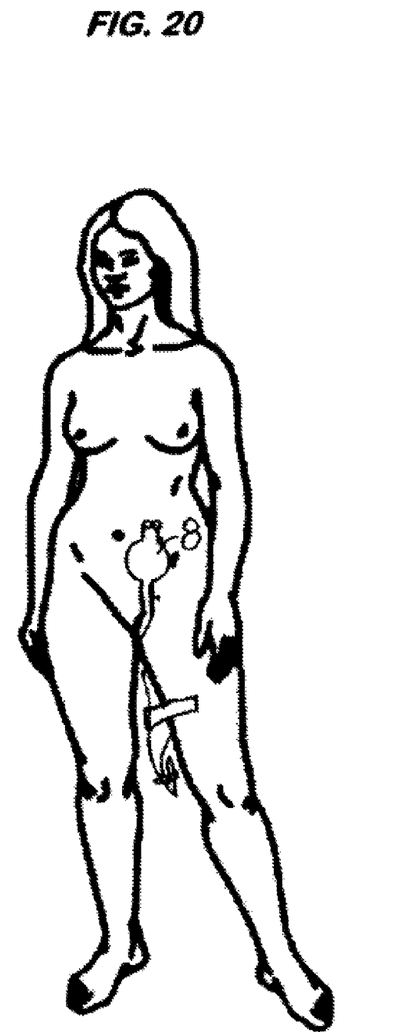
FIG. 20 shows the collection bag glued to a female patient's stomach.

The special design of the collection bag makes it possible for the bag to be folded 180 degrees in the patient's forward respective back direction. The above stated property allows for the bag to be used with lid 4, alternatively lid 8, to be glued on the patient's back. The same lid can be stuck on the patient's stomach, as shown in FIG. 19 for the man and FIG. 20 for the woman. The lid pasted on the back occurs when the health workers are attending to the patient see FIG. 18. The lid glued on the stomach is used when the patient can and wants to empty their faecal/urine bag.

Figure 6:
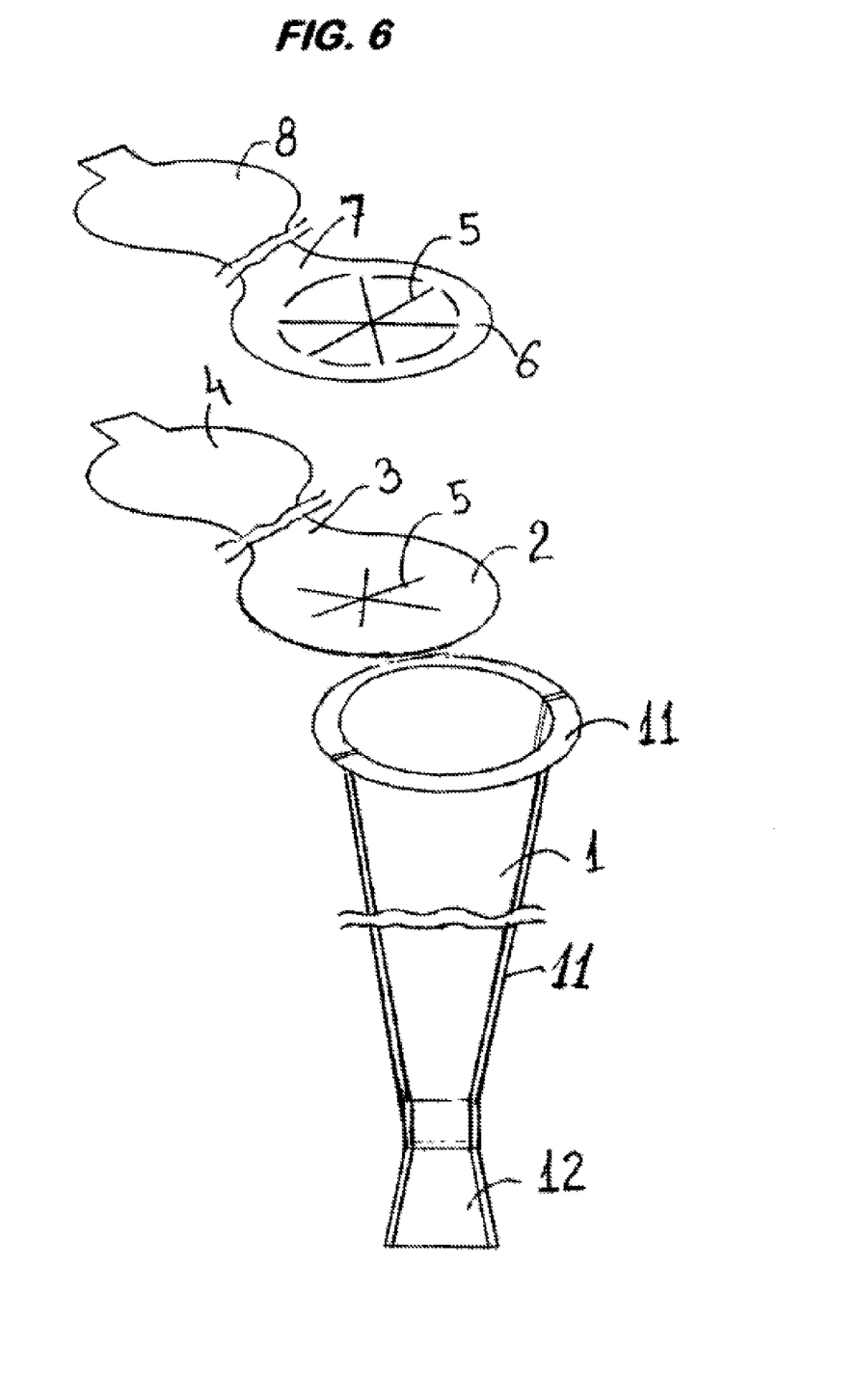
FIG. 6 shows in perspective, the collection bag's components (the funnel-like bag, the slotted top, carrying strap and lid), the components having been welded/glued together according to a specific pattern, forming channels for water rinsing, hot air blowing and the application of skin ointment.

FIG. 6 shows the collection bag's constituent parts. The bag is formed of two flat sheets 1 made of suitable thermoplastic film and whose exterior parts 11 are heat sealed/welded or glued to each other and against the periphery of a top 2. (Later called the lower top).

The lower top 2 has been provided with slits 5 and is connected via the lower carrying strap 3 with the lower lid 4.

The bag designed according to this method is suitable for one day's use. It can easily be sealed, transported and rinsed for later re-use, after an appropriate adhesive on the lower top 2 also the lower lid 4 have been replaced.

Figure 8:
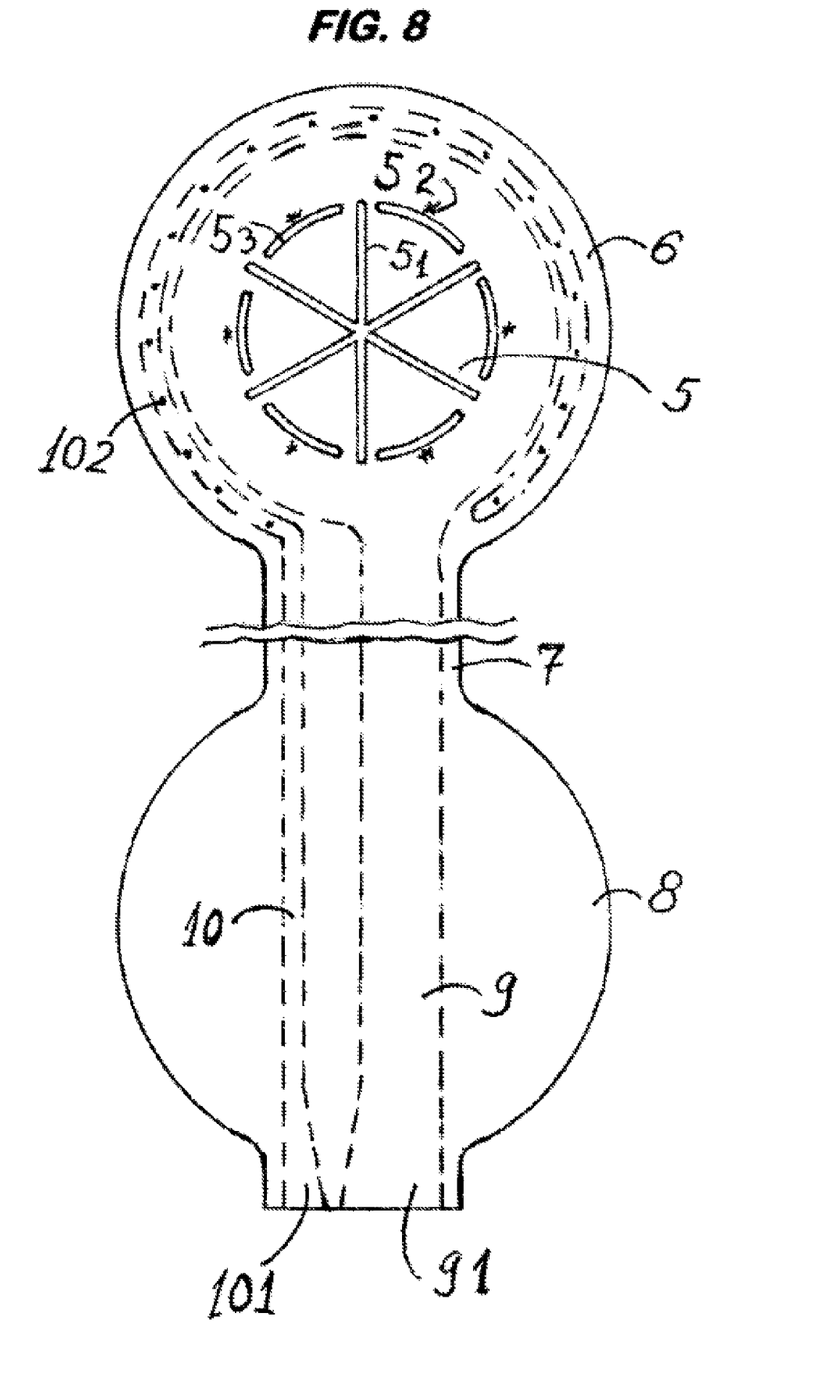
FIG. 8 shows a view of the slotted top with a carrying strap and all the channels illustrated.

The collection bag in FIG. 6 shows the same bag, but where the lower top 2 of the bag has been given an additional, and identical first top (later called the upper top) 6, a upper carrying strap 7 and upper lid 8 which are heat sealed/welded or glued to the lower top 2,3 and 4 according to FIG. 8.

By connecting the lower top 2,3,4 with the upper top 5,7,8 along the dotted lines (shown in FIG. 8) a rinse channel is formed 9 with the conical connection 91 and a lubricating channel 10 with its conical connection 101. Both channels extend around the top flaps 5. Channel 10 can, via the holes 102 be used to apply an appropriate skin ointment after rinsing.

Channel 9 ends with openings 53 which at its outermost edge 52 is spot welded/bonded to the lower top 2. The upper top 6,7,8 are fitted with identical tabs 5, which at their periphery 51 are heated sealed/welded/bonded together with the tabs on the lower top 2.

Figure 9:
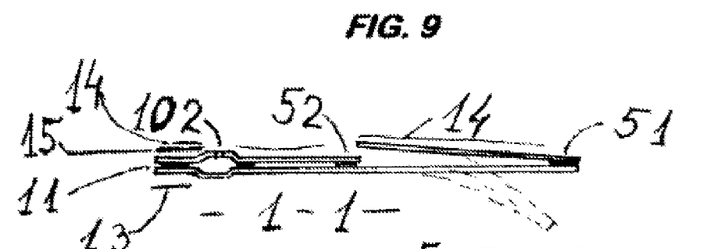
FIG. 9 shows a detailed section of the slotted top flap in unaffected condition.

FIG. 9 shows section 1-1 through a flap in unaffected state.

Figure 10:
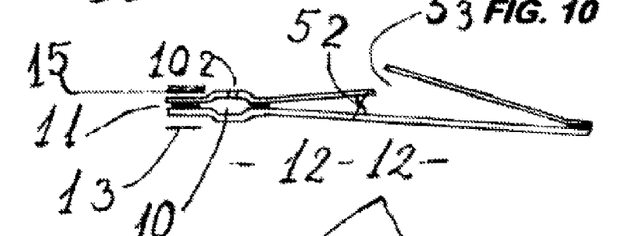
FIG. 10 shows a detailed section of the slotted top flap in affected state, where the flap has been exposed to water/air pressure.
Figure 11:
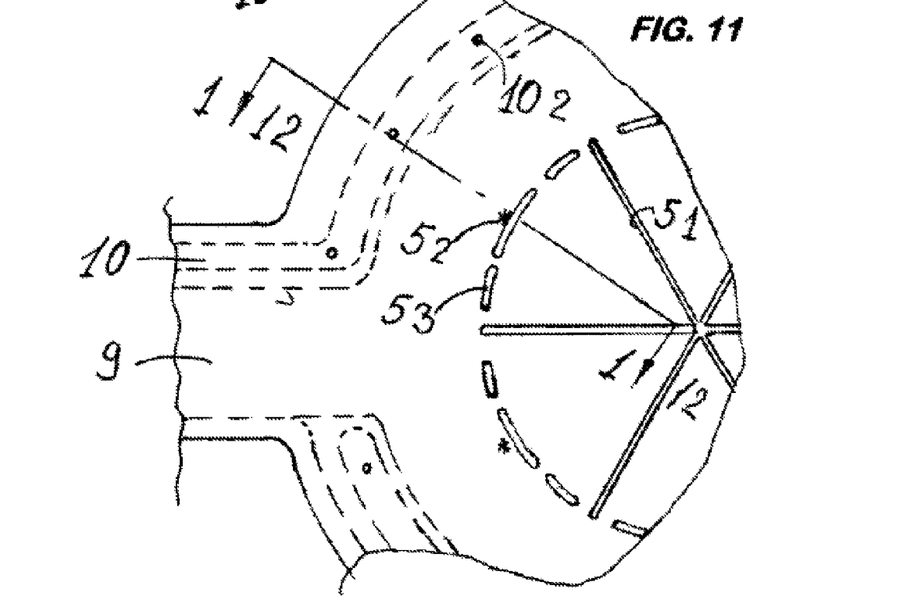
FIG. 11 shows a portion of the slotted top and its flaps where each weld/bonded joint is shown in a view from above.

FIG. 10 shows section 12-12 of the same flap at rinsing. When water flows through the channel 9 against the self-closing flap 5, the water pressure will open the flap opening 53 so that water flows onto the skin and in this way thoroughly rinse the patient.

After rinsing, hot air is passed through the same channel 9, thereby drying the patient. Skin ointment can then be applied to the patient via channel 10 and the openings 102.

The above stated procedure enables the patient to use the same collection bag for several days.

Figure 7:
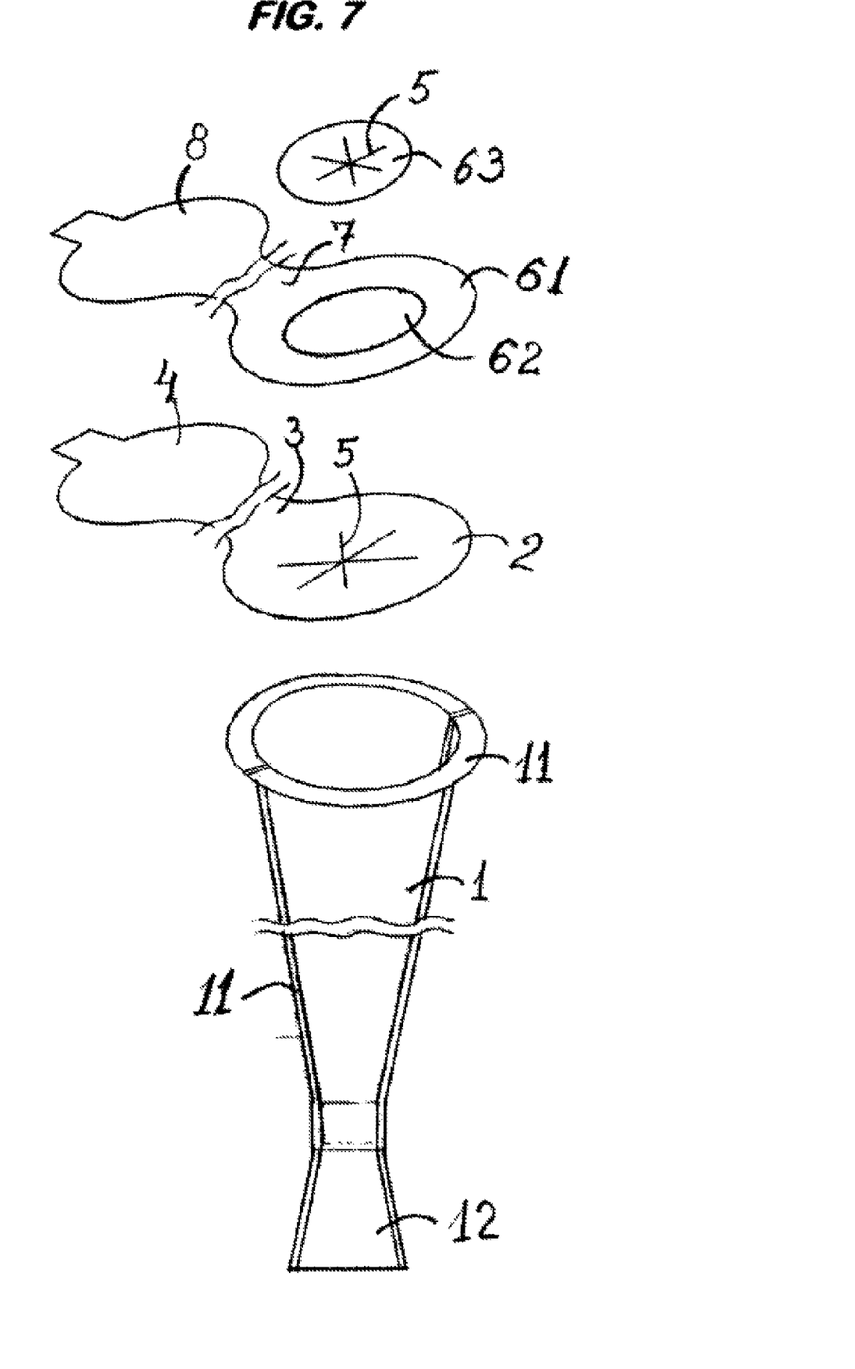
FIG. 7 shows in perspective one of the alternative designs for the collection bag and its components.

FIG. 7 shows an alternative design for the top of the collection bag, namely that the upper top 61 has been supplemented with an additional slotted upper top 63.

Figure 12:
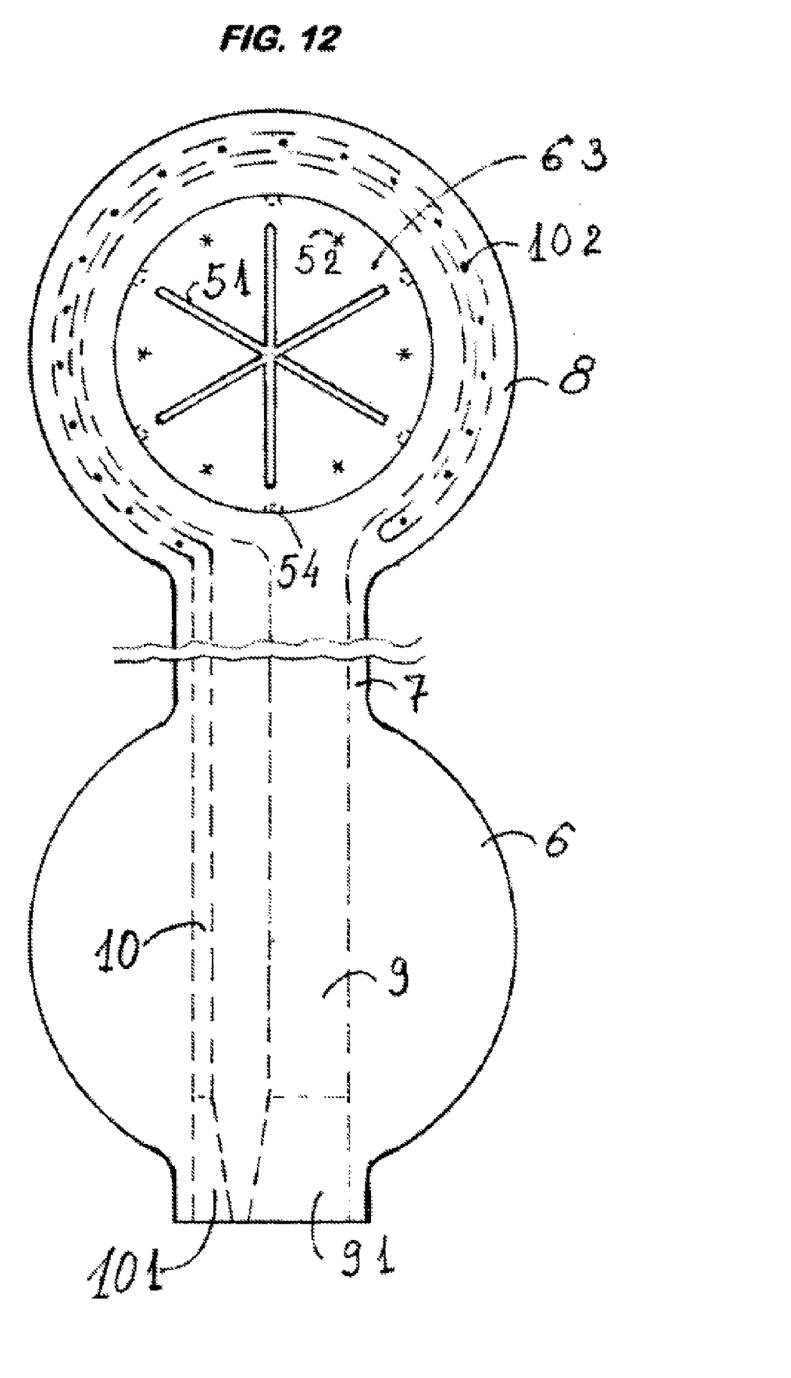
FIG. 12 shows in a view from above of an alternative design of the slotted top, carrying strap and lid.

The upper top 61, 7, 8 has been provided with an opening 62 that is covered with a slotted upper top 63. FIG. 12 shows the slotted upper top 63 from above.

The flaps on the upper top 63 are similar to the flaps on the lower top 2,3,4, and its edges 51 are heat sealed/welded or glued to each other.

Figure 13:
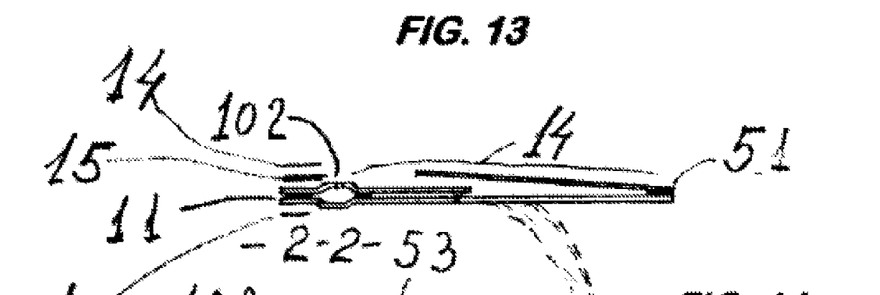
FIG. 13 shows an alternative view of the slotted top flap in unaffected condition.
Figures 14, 15:
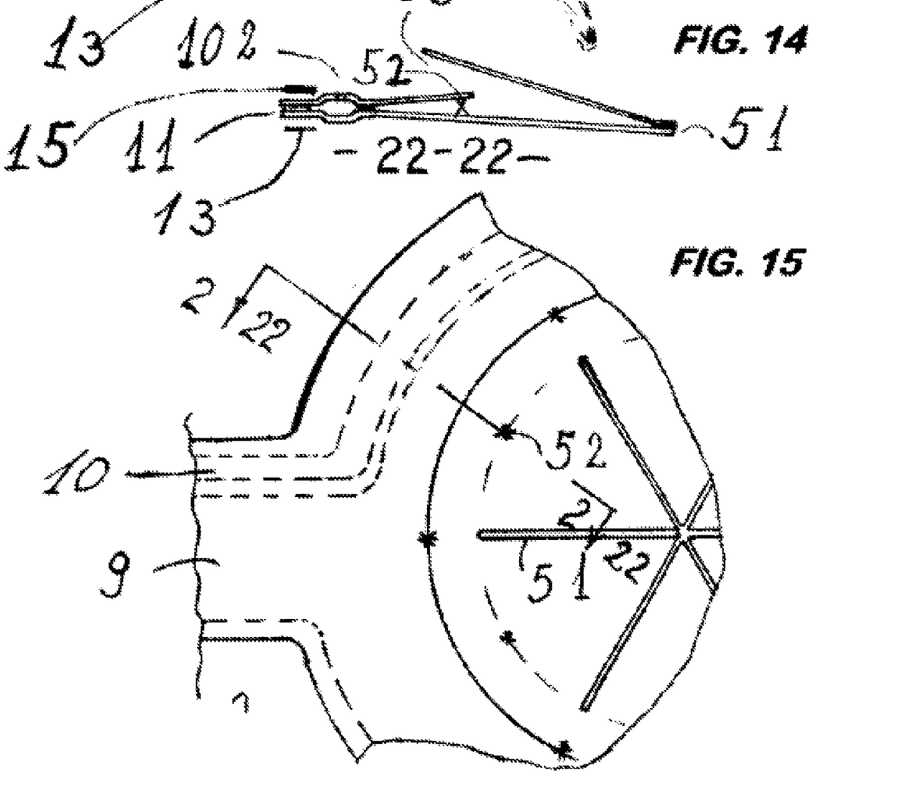
FIG. 14 shows an alternative view of the design of the slotted flap peak, in the affected state, after the flap has been exposed to water/air pressure.
FIG. 15 shows a part of the slotted top, with its flaps and the respective welding/gluing points in a view from above.

The upper top 63 is secured via points 54 to the upper lid 61. The upper top's opening 62 is via points 52 attached to the lower top 2 as shown in FIG. 13 and FIG. 14.

The above figures also show a light-restricting sheet 13 stuck on the underside of the lower top 2. Sheet 13 is to protect the light-sensitive adhesives that have been applied to the lower top 2 and also on the upper top 6.

Before removing the collection bag from the patient, the light-restricting sheet 13 is first removed from the underside of the lower top 2.

Thereafter, the skin attached surface of lower top 2 or upper top 6 is illuminated with a suitable light source for a few seconds after which the collection bag will loosen painlessly and can then be sealed with the lower lid 4 or the upper lid 8.

FIG. 13 and FIG. 14 also show a sheet 14 that can be whole covering, or divided into smaller parts, and that provides glue protection for the upper top 6, the upper carrying strap 7 and the upper lid 8.

Sheet 14 is made of a non-transparent material and is covered with a wax/silicone or similar coating for easy removal from the above mentioned adhesive coating on the top, carrying strap and lid.

Sheet 14 is also applied to the collection bag in the simplest execution, where the lower top 2 lower carrying strap 3 and lower lid 4 conclude the collection bag. Sheet 14 is also applied to the collection bag with the extra upper lid 63 to keep the adhesives light protected.

The light-sensitive glue can also be applied to a separate, ring-shaped, spongy, and transparent sheet 15 on one side, and a stronger glue on the other side so that the exchange of glue surface on the lower top 2 or upper top 6 can be done very quickly with good adhesion to the respective top. Sheet 15 is shown in FIG. 9 and FIG. 10, and FIG. 13 and FIG. 14 respectively.

When the water/air pressure, applied via channel 9 influences the self-closing flaps 5, the jets of water are able to be controlled via the extra upper top 63 against the skin, at the contact point of the glue against the collection bag's top and the patient's body.

The jets of water will therefore be effective in rinsing all parts of the skin's surface. After rinsing, the skin is dried using hot air, which is blown through the same Water/air channel 9.

The dry skin is treated with skin ointment from the tube T, which is distributed via channel 10 and the openings 102.

The treatment described above ensures good, hygienic and healthy treatment of the patient regardless of whether it is health workers who carry out the procedure, or whether it is the patients performing the procedure themselves.

The collection bag's slotted flaps 5 are so arranged on the upper top 6 of the bag that the bag can be used, without adjustment, for both male and female patients.

Figure 16:
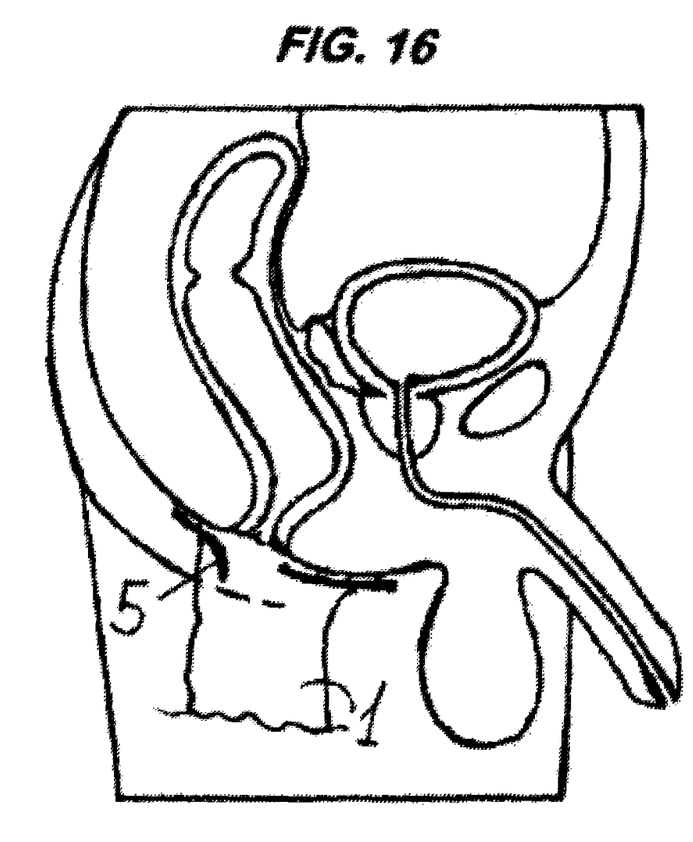
FIG. 16 shows the collection bag's top glued to a male patient.

FIG. 16 shows the collection bag's affected rear flaps 5 re male patients.

Figure 17:
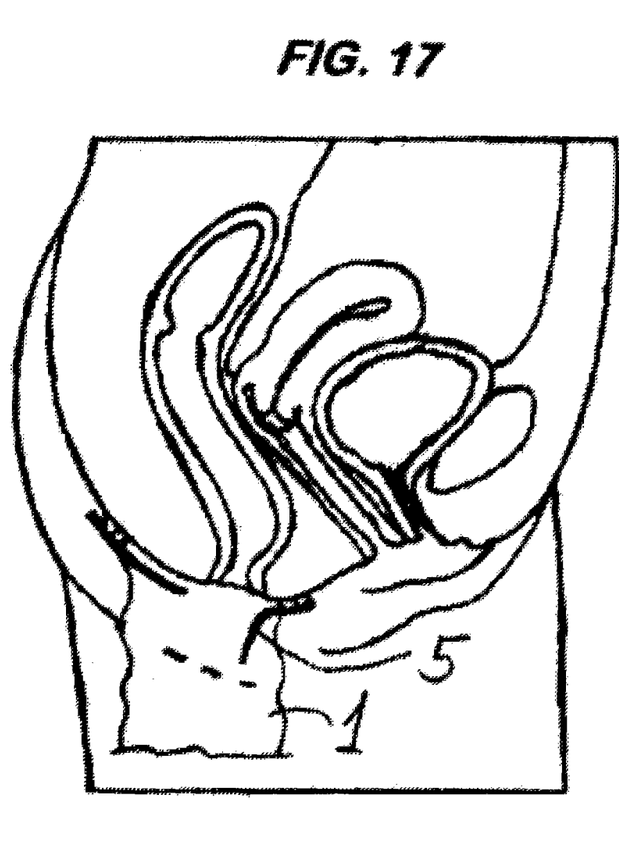
FIG. 17 shows the collection bag's top glued to a female patient.

FIG. 17 shows the collection bag's affected forward flaps re female patients.

Another feature of the collection bag is the existence of a replaceable odor removal filter F that is attached to the upper lid 8's conical channel opening 91.

The collection bag can be made from a suitable thermoplastic film or laminated film.

Since the invention has been described in detail above to illustrate the invention and a couple of variants, it should be clear to professionals that many of the aforementioned details may be varied within the invention's field of reference.

The invention claimed is:

1. An apparatus for collecting fecal or urinary waste comprising:
    a bag formed of similar thermoplastic sheets, said bag having an inverted funnel formed at one end thereof, said inverted funnel having a removable spongeous stopper therein and a hose clamp extending therearound;
    a first layer affixed to a tapered-most end of said bag, said first layer having a self-closing flap extending radially from a surface thereof;
    a second layer affixed over said first layer at said opposite side of said bag, said second layer having a self-closing flap extending radially from a surface thereof, said second layer having a plurality of slits and apertures thereon;
    a first strap affixed to said first layer and extending outwardly therefrom, said first strap having a first lid affixed thereto;
    a second strap affixed to said second layer and extending outwardly therefrom, said second strap having a second lid affixed thereto, said second lid of said second strap being insertable into said first layer so as to define a rinse channel and a skin-ointment channel in the form of a conical funnel;
    a deodorizing filter fitted into said conical funnel;
    an adhesive applied to a periphery of said second layer; and
    a cover sheet removably placed over said adhesive.

2. The apparatus of claim 1, wherein at least one of said first layer and second layer is formed of a transparent material, one of said first layer and second layer is covered with an adhesive, at least one of said first layer and second layer is covered by at least one opaque cover sheet.

3. The apparatus of claim 1, wherein said self-closing flap is formed by a separate thermoplastic sheet connected to said second layer, said self-closing flap is affixed to tabs on said first layer.

* * * * *